US010898607B2

(12) United States Patent
Van Epps et al.

(10) Patent No.: US 10,898,607 B2
(45) Date of Patent: Jan. 26, 2021

(54) BIOERODIBLE MATRIX FOR TISSUE INVOLVEMENT

(71) Applicant: Allergan, Inc., Irvine, CA (US)

(72) Inventors: Dennis E. Van Epps, Goleta, CA (US); Thomas E. Powell, Santa Barbara, CA (US)

(73) Assignee: ALLERGAN, INC., Irvine, CA (US)

( * ) Notice: Subject to any disclaimer, the term of this patent is extended or adjusted under 35 U.S.C. 154(b) by 110 days.

(21) Appl. No.: 15/373,666

(22) Filed: Dec. 9, 2016

(65) Prior Publication Data

US 2017/0087273 A1 Mar. 30, 2017

Related U.S. Application Data

(60) Continuation of application No. 14/189,457, filed on Feb. 25, 2014, now abandoned, which is a continuation of application No. 13/453,886, filed on Apr. 23, 2012, now abandoned, which is a division of application No. 12/705,177, filed on Feb. 12, 2010, now abandoned.

(60) Provisional application No. 61/164,344, filed on Mar. 27, 2009.

(51) Int. Cl.
| | | |
|---|---|---|
| *A61L 27/18* | (2006.01) | |
| *A61L 27/38* | (2006.01) | |
| *A61L 27/56* | (2006.01) | |
| *A61L 27/58* | (2006.01) | |
| *A61L 27/36* | (2006.01) | |
| *A61F 2/12* | (2006.01) | |
| *A61L 27/34* | (2006.01) | |

(52) U.S. Cl.
CPC ............... *A61L 27/18* (2013.01); *A61F 2/12* (2013.01); *A61L 27/34* (2013.01); *A61L 27/3604* (2013.01); *A61L 27/3804* (2013.01); *A61L 27/3834* (2013.01); *A61L 27/3886* (2013.01); *A61L 27/56* (2013.01); *A61L 27/58* (2013.01); *A61L 2420/06* (2013.01); *A61L 2430/04* (2013.01)

(58) Field of Classification Search
None
See application file for complete search history.

(56) References Cited

U.S. PATENT DOCUMENTS

| | | | |
|---|---|---|---|
| 4,282,954 A | 8/1981 | Hill | |
| 4,533,568 A | 8/1985 | McClinton et al. | |
| 4,605,691 A | 8/1986 | Balazs et al. | |
| 4,655,777 A * | 4/1987 | Dunn | A61L 27/44 424/423 |
| 5,458,653 A * | 10/1995 | Davidson | A61F 2/30767 623/23.36 |
| 5,716,404 A | 2/1998 | Vacanti | |
| 5,972,385 A | 10/1999 | Liu et al. | |
| 6,129,761 A | 10/2000 | Hubbell et al. | |
| 6,753,311 B2 * | 6/2004 | Fertala | A61K 9/0009 514/17.2 |
| 6,777,231 B1 | 8/2004 | Katz et al. | |
| 6,991,652 B2 | 1/2006 | Burg et al. | |
| 7,129,209 B2 | 10/2006 | Rhee et al. | |
| 7,316,822 B2 | 1/2008 | Binette et al. | |
| 7,767,452 B2 | 8/2010 | Kleinsek et al. | |
| 7,799,767 B2 | 9/2010 | Lamberti et al. | |
| 7,875,296 B2 | 1/2011 | Binette et al. | |
| 7,972,628 B2 | 7/2011 | Ratner et al. | |
| 8,053,423 B2 | 11/2011 | Lamberti et al. | |
| 8,066,691 B2 | 11/2011 | Khouri | |
| 8,137,702 B2 | 3/2012 | Binette et al. | |
| 8,153,591 B2 | 4/2012 | Masters et al. | |
| 8,246,947 B2 | 8/2012 | Hedrick et al. | |
| 8,288,347 B2 | 10/2012 | Collette et al. | |
| 8,562,677 B2 | 10/2013 | Job | |
| 8,679,279 B2 | 3/2014 | Thompson et al. | |
| 8,746,014 B2 | 6/2014 | Mortarino | |
| 9,011,333 B2 | 4/2015 | Geissler et al. | |
| 9,044,897 B2 | 6/2015 | Manesis et al. | |
| 9,155,613 B2 | 10/2015 | Thompson et al. | |
| 9,204,953 B2 | 12/2015 | Mortarino | |
| 9,204,954 B2 | 12/2015 | Mortarino | |
| 9,205,238 B2 | 12/2015 | Ledergerber | |
| 9,326,840 B2 | 5/2016 | Mortarino | |

(Continued)

FOREIGN PATENT DOCUMENTS

| | | |
|---|---|---|
| CA | 2811975 | 11/2011 |
| CA | 2975348 | 8/2015 |

(Continued)

OTHER PUBLICATIONS

Bengtson, Bradley et al., Style 410 Highly Cohesive Silicone Breast Implant Core Study Results at 3 Years, Plast. Reconstr. Surg., 2007, 40S-48S, 120(1).
Gamboa-Bobadilla, Mabel et al., Implant Breast Reconstruction Using Acellular Dermal Matrix, Ann Plast Surg, 2006, 22-25, 56.
Halbleib, Melanie et al., Tissue Engineering of White Adipose Tissue Using Hyaluronic Acid-Based Scaffolds. I: in vitro Differentiation of Human Adipocyte Precursor Cells on Scaffolds, Biomaterials, 2003, 3125-3132, 24.
Karsten Hemmrich, et al., Autologous In Vivo Adipose Tissue Engineering in Hyaluronan-Based Gels—A Pilot Study, Journal of Surgical Research, 2008, 82-88, 144, US.

(Continued)

*Primary Examiner* — Blaine Lankford
(74) *Attorney, Agent, or Firm* — Nathan S. Smith; Sujohn Das; Morgan, Lewis & Bockius LLP

(57) ABSTRACT

Disclosed herein are polyurethane polymer matrices with a porosity of from about 20 microns to about 90 microns that are useful in promoting closure and protection of incision sites; supporting the lower pole position of breast implants; and providing a partial or complete covering of breast implants to provide a beneficial interface with host tissue and to reduce the potential for malpositioning or capsular contracture. The disclosed matrices can be seeded with mammalian cells.

8 Claims, No Drawings

(56) References Cited

U.S. PATENT DOCUMENTS

| | | |
|---|---|---|
| 9,593,224 B2 | 3/2017 | Liu et al. |
| 9,673,516 B2 | 6/2017 | Mejia |
| 9,688,006 B2 | 6/2017 | Nieto et al. |
| 9,750,600 B2 | 9/2017 | Mayo |
| 9,901,438 B2 | 2/2018 | Mejia et al. |
| 10,111,744 B2 | 10/2018 | Mora et al. |
| 10,176,412 B2 | 1/2019 | Geissler et al. |
| 2004/0058056 A1* | 3/2004 | Osaki ............. A61L 31/06 427/2.1 |
| 2004/0266992 A1 | 12/2004 | Migliaresi et al. |
| 2005/0142162 A1 | 6/2005 | Hunter et al. |
| 2006/0293760 A1 | 12/2006 | DeDeyne |
| 2007/0104693 A1 | 5/2007 | Quijano et al. |
| 2007/0251531 A1 | 11/2007 | Khouri |
| 2008/0153476 A1* | 6/2008 | Jang ............. G08C 17/00 455/420 |
| 2008/0300681 A1 | 12/2008 | Rigotti et al. |
| 2009/0098177 A1 | 4/2009 | Werkmeister et al. |
| 2009/0123547 A1 | 5/2009 | Hill |
| 2009/0124552 A1 | 5/2009 | Hill |
| 2009/0162415 A1 | 6/2009 | Huang et al. |
| 2009/0181104 A1 | 7/2009 | Rigotti |
| 2009/0196901 A1 | 8/2009 | Guilak et al. |
| 2009/0317376 A1 | 12/2009 | Zukowska et al. |
| 2010/0160948 A1 | 6/2010 | Rigotti et al. |
| 2010/0161052 A1 | 6/2010 | Rigotti et al. |
| 2010/0168780 A1 | 7/2010 | Rigotti et al. |
| 2011/0008406 A1 | 1/2011 | Altman et al. |
| 2011/0008436 A1 | 1/2011 | Altman et al. |
| 2011/0008437 A1 | 1/2011 | Altman et al. |
| 2011/0014263 A1 | 1/2011 | Altman et al. |
| 2011/0014287 A1 | 1/2011 | Altman et al. |
| 2011/0020409 A1 | 1/2011 | Altman et al. |
| 2011/0052695 A1 | 3/2011 | Jiang et al. |
| 2011/0070281 A1 | 3/2011 | Altman et al. |
| 2011/0097381 A1 | 4/2011 | Binette |
| 2011/0111031 A1 | 5/2011 | Jiang et al. |
| 2011/0150823 A1 | 6/2011 | Huang |
| 2011/0150846 A1 | 6/2011 | Van Epps et al. |
| 2011/0183001 A1 | 7/2011 | Rosson et al. |
| 2011/0189292 A1 | 8/2011 | Lebreton et al. |
| 2012/0010146 A1 | 1/2012 | Han et al. |
| 2012/0029537 A1 | 2/2012 | Mortarino |
| 2012/0045420 A1 | 2/2012 | Van Epps et al. |
| 2012/0076868 A1 | 3/2012 | Lamberti et al. |
| 2012/0156265 A1 | 6/2012 | Binette et al. |
| 2012/0164116 A1 | 6/2012 | Van Epps et al. |
| 2012/0165935 A1 | 6/2012 | Van Epps |
| 2012/0171265 A1 | 7/2012 | Altman et al. |
| 2012/0172317 A1 | 7/2012 | Altman et al. |
| 2012/0172985 A1 | 7/2012 | Altman et al. |
| 2012/0213852 A1 | 8/2012 | Van Epps et al. |
| 2012/0213853 A1 | 8/2012 | Van Epps et al. |
| 2012/0219627 A1 | 8/2012 | Van Epps et al. |
| 2012/0232652 A1 | 9/2012 | Mora et al. |
| 2012/0263686 A1 | 10/2012 | Van Epps et al. |
| 2012/0265297 A1 | 10/2012 | Altman et al. |
| 2012/0269777 A1 | 10/2012 | Van Epps et al. |
| 2015/0282926 A1 | 10/2015 | Chacon et al. |
| 2016/0130690 A1 | 5/2016 | Winn et al. |
| 2017/0049549 A1 | 2/2017 | Bayat et al. |
| 2017/0256850 A1 | 9/2017 | Mejia |
| 2017/0290652 A1 | 10/2017 | Nieto et al. |
| 2018/0200043 A1 | 7/2018 | Mejia et al. |
| 2018/0360594 A1 | 12/2018 | Schuessler et al. |
| 2019/0029807 A1 | 1/2019 | Nieto et al. |

FOREIGN PATENT DOCUMENTS

| | | |
|---|---|---|
| CA | 3007138 | 6/2017 |
| CA | 3013698 | 8/2017 |
| CA | 3019747 | 10/2017 |
| CA | 3020876 | 10/2017 |
| CA | 3023507 | 11/2017 |
| CN | 104837441 | 8/2015 |
| CN | 108697337 | 10/2018 |
| CN | 109069251 | 12/2018 |
| CN | 109152531 | 1/2019 |
| CN | 109152640 | 1/2019 |
| EP | 0419134 | 3/1991 |
| EP | 1405649 A1 | 4/2004 |
| EP | 1796595 | 6/2007 |
| EP | 2446858 | 5/2012 |
| EP | 2568875 | 3/2013 |
| EP | 2895994 | 7/2015 |
| EP | 2921137 | 9/2015 |
| EP | 2931490 | 10/2015 |
| EP | 2962662 | 1/2016 |
| EP | 3107487 | 12/2016 |
| EP | 3383314 | 10/2018 |
| EP | 3413788 | 12/2018 |
| EP | 2895109 B1 | 1/2019 |
| EP | 3439543 | 2/2019 |
| EP | 3442468 | 2/2019 |
| EP | 3443933 | 2/2019 |
| EP | 2227175 B1 | 3/2019 |
| ES | 2409691 | 6/2013 |
| KR | 20180103873 | 9/2018 |
| KR | 20180116302 | 10/2018 |
| KR | 20180134358 | 12/2018 |
| KR | 20180137503 | 12/2018 |
| KR | 20190008252 | 1/2019 |
| WO | 2008100534 | 8/2008 |
| WO | 2008148026 A1 | 12/2008 |
| WO | 2009-022133 A2 | 2/2009 |
| WO | 2011072399 A1 | 6/2011 |
| WO | WO 2011/143324 | 11/2011 |
| WO | WO 2014/043631 | 3/2014 |
| WO | WO 2014/047013 | 3/2014 |
| WO | WO 2014/076339 | 5/2014 |
| WO | WO 2015/121686 | 8/2015 |
| WO | WO 2017/093528 | 6/2017 |
| WO | WO 2017/137853 | 7/2017 |
| WO | WO 2017/175055 | 10/2017 |
| WO | WO 2017/181144 | 10/2017 |
| WO | WO 2017/184962 | 10/2017 |
| WO | WO 2017/196973 | 11/2017 |
| WO | WO 2018/078446 | 5/2018 |
| WO | WO 2018/188930 | 10/2018 |

OTHER PUBLICATIONS

Seung-Woo Cho, Engineering of Volume Stable Adipose Tissue, Biomaterials, 2005, 3577-3585, 26, Elsevier, US.

Stillaert, et al., Human Clinical Experience with Adipose Precursor Cells Seeded on Hyaluronic Acid-Based Spongy Scaffolds, Biomaterials, 2008, 3953-3959, 29, Elsevier.

* cited by examiner

BIOERODIBLE MATRIX FOR TISSUE INVOLVEMENT

RELATED APPLICATION

This application is a continuation of U.S. patent application Ser. No. 14/189,457 filed on Feb. 25, 2014, which is a continuation of Ser. No. 13/453,886, filed on Apr. 23, 2012, now abandoned, which is a divisional of U.S. patent application Ser. No. 12/705,177, filed on Feb. 12, 2010, now abandoned, which claims priority to U.S. provisional patent application 61/164,344, filed Mar. 27, 2009, the entire disclosure of each of these applications being incorporated herein by this reference.

FIELD OF THE INVENTION

The present invention generally relates to medical implants for reconstruction, augmentation and/or wound healing and more specifically relates to such implants including a polymer component and a cellular component.

BACKGROUND OF THE INVENTION

Often following damage such as a surgical incision, skin can benefit from additional support to promote wound healing. This is in part because spontaneous recovery can require a long period of time and pain can continue throughout the repair process.

Repair of soft tissue defects also is critical following reconstructive and augmentative surgeries. For example, more than 250,000 reconstructive procedures are performed on the breast each year. Women afflicted with breast cancer, congenital defects or damage resulting from trauma have very few alternatives to reconstruction. Surgery of the breast can also be cosmetic. Cosmetic surgeries include augmentation, for example, using implants; reduction; and reconstruction.

Mesh or matrix materials are generally used to provide strength to fascia and soft tissue weakened by surgery or to provide lift to soft tissue for reconstructive or cosmetic purposes. There are basically two types of mesh or matrix materials used surgically for these purposes, synthetic fiber meshes and natural or modified organic or animal derived matrix materials. In the synthetic fiber category, polypropylene, polyester and polytetrafluoroethylene have been the primary materials used and are sold by a number of different companies with variations in pore size and weight. Current versions of the synthetic materials have incorporated coatings or modifications of the fibers to enhance biocompatibility. These current materials used to promote wound healing or for soft tissue reconstruction or augmentation, however, still suffer from shortcomings such as suboptimal volume retention, donor site morbidity, and in some instances, continued poor biocompatibility.

Accordingly, it is desirable to promote wound healing and soft tissue reconstruction or augmentation by providing a suitable matrix material for these purposes.

SUMMARY OF THE INVENTION

The present invention is generally directed to bioresorbable or bioerodible polymer implants useful in reconstructive surgical procedures, augmentation surgical procedures, promotion of wound healing, and closure and protection of incision sites, without limitation thereto.

Advantageously, the present implants are structured to be useful in conjunction with traditional breast implants, for example, for supporting the lower pole position of breast implants. Further, the present implants may be used to provide a partial or complete covering of breast implants, for example, traditional or conventional breast implants. In this case, the present implants may be effective in providing a beneficial interface with host tissue thereby reducing the potential for malpositioning or capsular contracture.

More specifically, the present implants comprise a polymer component, for example, an resorbable or erodible material in the form of a matrix (hereinafter, sometimes, "bioerodible or bioresorbable matrix") comprising, for example, a polyurethane formulation. The matrix may comprise polycaprolactone, for example, soft segments of polycaprolactone, or another suitable material. In specific embodiments, the matrices are at least one or more of the following: biocompatible, resistant to loads experienced during surgical implant; pliable, porous, sterilizable, remoldable, for example, by invading tissue, and erodible or resorbable as new tissue is formed.

The matrices may be porous. For example, in some embodiments, the matrices have a porosity of between about 20 microns and about 350 microns. The porous matrices can be seeded with stem cells or progenitor cells prior to or during implantation in the body. When seeded with cells, the matrices may have an enhanced effectiveness in replacement thereof with the patient's own viable tissue.

There are many potential particular uses of the disclosed matrices. The disclosed matrices can promote wound healing and soft tissue reconstruction or augmentation by providing strength and covering for incisions and/or by providing support and a substrate for tissue in-growth and for growth of cells seeded on the matrix. Particularly, the disclosed matrices can comprise interconnecting cells or a fibrous network with enough strength to provide closure and protection of incision sites. The matrices can also support the lower pole position of breast implants or be used for mastopexy. Additionally the matrices can be used as a partial or complete covering of breast implants to provide a beneficial interface with host tissue and to reduce the potential for malpositioning or capsular contracture.

Following implantation, the disclosed matrices can be absorbed into the body over time. This absorption can coincide as infiltrating tissue replaces the matrix material. Thus, the matrix can provide temporary scaffolding and well-defined structure during wound healing and soft tissue reconstruction or augmentation. The methods may further comprise the step of seeding the matrix with viable cellular material prior to or during implantation.

Also provided are methods of promoting wound healing or wound closure, for example, at an incision site. The methods generally comprise implanting a matrix, for example a bioerodible or bioresorbable polymer matrix as described elsewhere herein, at the wound or incision site and allowing the wound or incision to heal while the implant is eroded or absorbed in the body and is replaced with the patient's own viable tissue. The methods may further comprise the step of seeding the matrix with viable cellular material prior to or during implantation.

Methods of augmenting or reconstructing the breast of a human being are also provided. For example, a method is provided for enhancing support of a conventional breast implant, for example, enhancing support of the lower pole position of a breast implant. For example, the method generally comprises the steps of implanting a matrix, for example a bioerodible or bioresorbable polymer matrix as described elsewhere herein, near or in proximity to a breast implant, for example, a conventional breast implant, and seeding the matrix with viable cellular material prior to or during implantation.

The matrices can also be involved in a method of providing a beneficial interface between host tissue and a prostheses, for example, a breast implant. In some embodiments, the matrices are structured to be effective to reduce the potential for malpositioning or capsular contracture of breast implants. For example, methods are provided for augmenting or reconstructing a human breast, the methods generally comprising: providing a partial or complete covering of breast implants wherein the partial or complete covering comprises a matrix comprising a polymer, for example, a porous polymer as described elsewhere herein, and the porous polymer being seeded with viable cellular material. In some embodiments, the matrix is a wrap-like configuration on a conventional silicone or saline filled conventional breast implant. The methods may further comprise the step of seeding the matrix with viable cellular material prior to or during implantation.

The matrix material may comprise a woven or non-woven fabric material, for example, a fiber spun, unwoven fabric such as felt, or a foam material. As mentioned elsewhere herein, the matrix may be porous.

In some embodiments, the matrices can comprise a polyurethane polymer with a porosity of from about 20 microns to about 350 microns. In some embodiments, the matrix is a resorbable polyurethane polymer. In some embodiments, the matrices are polycaprolactone soft segments appropriately shaped for implantation at a surgical incision site.

In some embodiments of the invention, implants are provided which comprise a polymer component, for example, such as the bioerodible or bioresorbable polymer matrices described elsewhere herein, and a cellular component, for example, viable stem cells and adipose cells.

DETAILED DESCRIPTION OF THE INVENTION

Following damage, such as that caused by a surgical incision, skin can benefit from additional support to promote wound healing. Mesh or matrix materials are generally used to provide strength to fascia and soft tissue weakened by surgery or to provide lift to soft tissue for reconstructive or cosmetic purposes including breast reconstruction or mastopexy. Two types of mesh or matrix materials are commonly used surgically for these purposes: synthetic fiber meshes and natural or modified organic or animal derived matrix materials. These currently-used materials, however, still suffer from shortcomings such as suboptimal volume retention, donor site morbidity, and in some instances, continued poor biocompatibility.

Provided are resorbable matrices to provide strength and covering for incisions and soft tissue reconstruction or augmentation. The disclosed matrices can provide immediate strength to an incision site or soft tissue reconstruction or augmentation site and also provide a substrate for tissue in-growth. In certain embodiments, the disclosed matrix can comprise interconnecting cells or a fibrous network with enough strength to provide closure and protection of incision sites. The disclosed matrices can also support the lower pole position of breast implants or can be used as a partial or complete covering of breast implants to provide a beneficial interface with host tissue and to reduce the potential for malpositioning or capsular contracture. Ultimately the non-biologic resorbable material can be absorbed and the infiltrating tissue can replace the matrix. Thus, the matrix can provide temporary scaffolding and well-defined structure until it is no longer needed.

In one embodiment of the disclosed matrices, the matrices can comprise a bioerodible polyurethane formulation using polycaprolactone soft segments or another erodible material. In the case of polyurethane matrices, this porosity should be between about 20 microns and about 350 microns. Disclosed matrices can also be seeded with stem cells or progenitor cells to enhance the replacement of the matrices with viable tissue. In disclosed embodiments the porosity of the material can be adjusted to achieve optimal tissue interaction and viability.

In some embodiments of the invention, the matrix comprises a biocompatible, bioerodible material which possess sufficient mechanical properties to resist loads experienced during implantation into the patient. The material is pliable and porous to allow cell invasion or growth and is absorbed or degraded as new tissue is formed.

The present matrices in some embodiments comprise bioerodible biopolymers. As used herein, the term "biopolymer" is understood to encompass naturally occurring polymers, as well as synthetic modifications or derivatives thereof. Such biopolymers include, without limitation, hyaluronic acid, collagen, recombinant collagen, cellulose, elastin, alginates, chondroitin sulfate, chitosan, chitin, keratin, silk, small intestine submucosa (SIS), and blends thereof. These biopolymers can be further modified to enhance their mechanical or degradation properties by introducing cross-linking agents or changing the hydrophobicity of the side residues. Other suitable biocompatible, bioerodible polymers include, without limitation, aliphatic polyesters, polyalkylene oxalates, polyamides, polycarbonates, polyorthoesters, polyoxaesters, polyamidoesters, polyanhydrides, polyphosphazenes and polyurethanes. Any suitable aromatic or aliphatic diisocyanates can be used and are considered to be included within the scope of the present invention.

Polyurethane materials are generally synthesized by reacting polyisocyanates with polyols. In general, examples of polyols used include polyether polyols such as poly (ethylene oxide) and poly(propylene oxide), modified polyether polyols, polytetramethylene glycol, condensation polyester polyols produced by reacting dicarboxylic acids with diols, lactone-type polyester polyols produced by ring opening polymerization of .epsilon.-caprolactone or the like, and polycarbonate polyols.

When no additional protective agents are used in a polyurethane polymer, the effect of moisture causes the pure polyester polyurethanes having the polyol component based on adipic acid and glycol to be hydrolytically degraded. The polyester component in the soft segment is saponified by water, and the polyurethane chains split into shorter units. This degradation occurs even under mild conditions, i.e., at temperatures and at an atmospheric humidity.

In one embodiment, a polyurethane polymer with beneficial characteristics is obtained by reacting about 100 parts by weight of a polyol mixture with 1,6-hexamethylene diisocyanate, isophorone diisocyanate or dicyclohexylmethane 4,4'-diisocyanate and diol-chain-lengthening means. The NCO coefficient, formulated from the quotients of the equivalency ratios of isocyanate groups multiplied by 100 and of the sum of the hydroxyl groups from the polyol mixture and the chain-lengthening means, is from about 97 to about 99. The polyol mixture consists of about 70 to about 90 parts by weight of polyester polyol having a molecular weight of about 2000, based on adipic acid with ethane diol, butane diol, hexane diol, diethylene glycol or neopentyl glycol, as well as of about 10 to about 30 parts by weight of polyether polyol on the basis of polyethylene glycol having a molecular weight of about 800 to about 4000. The chain lengthening means can be 1,4-butane diol and/or 1,6-hexane diol. The 1,6-hexamethylene diisocyanate, isophorone diisocyanate or dicyclohexylmethane diisocyanate can be present in an equivalency ratio to the polyol mixture of about 2.8:1.0 to about 12.0:1.0. The chain lengthening means can be present in an equivalency ratio to the polyol mixture of about 1.75:1.0 to about 11.3:1.0.

The polyol mixture for preparing polyurethane polymers used in the disclosed matrices can contain, on the one hand, about 70 to about 90 parts by weight of polyester polyol having a molecular weight of about 2000, on the basis of adipic acid with ethane diol or with butane diol, hexane diol, diethylene glycol or neopentyl glycol. On the other hand, the polyol mixture can contain about 10 to about 30 parts by weight of polyether polyol on the basis of polyethylene glycol having a molecular weight of about 800 to about 4000.

In an equivalency ratio of about 2.8:1.0 to about 12.0:1.0 to the polyol mixture, the polyurethane compound contains, in addition, 1,6-hexamethylene diisocyanate, isophorone diisocyanate or dicyclohexylmethane 4,4'-diisocyanate.

Serving as chain lengtheners can be 1,4-butane diol or 1,6-hexane diol, alternately or in combination, in an equivalency ratio to the polyol mixture of about 1.75:1.0 to about 11.3:1.0. The NCO coefficient, formulated from the quotients of the equivalency ratios of isocyanate groups multiplied by 100 and the sum of the hydroxyl groups from the polyol combination and the chain lengthener can amount to about 97 to about 99.

When aliphatic polyesters are used in making the disclosed matrices, the aliphatic polyesters can be homopolymers or copolymers (random, block, segmented, tapered blocks, graft, triblock, etc.) having a linear, branched or star structure. Suitable monomers for making aliphatic homopolymers and copolymers include, but are not limited to, lactic acid, lactide (including L-, D-, meso and L,D mixtures), glycolic acid, glycolide, ε-caprolactone, p-dioxanone, trimethylene carbonate, Δ-valerolactone, β-butyrolactone, ε-decalactone, 2,5-diketomorpholine, pivalolactone, α,α-diethylpropiolactone, ethylene carbonate, ethylene oxalate, 3-methyl-1,4-dioxane-2,5-dione, 3,3-diethyl-1,4-dioxan-2,5-dione, γ-butyrolactone, 1,4-dioxepan-2-one, 1,5-dioxepan-2-one, 6,6-dimethyl-dioxepan-2-one and 6,8-dioxabicyclooctane-7-one.

Elastomeric copolymers also are appropriate for use in making the disclosed matrices. Suitable elastomeric polymers include those with an inherent viscosity in the range of about 1.2 dL/g to about 4 dL/g, in the range of about 1.2 dL/g to about 2 dL/g and in the range of about 1.4 dL/g to about 2 dL/g, as determined at 25° C. in a 0.1 gram per deciliter (g/dL) solution of polymer in hexafluoroisopropanol (HFIP). Further, suitable elastomers exhibit a high percent elongation and a low modulus, while possessing good tensile strength and good recovery characteristics. In particular disclosed embodiments, the elastomer from which the matrix is formed exhibits a percent elongation greater than about 200 percent or greater than about 500 percent. In addition to these elongation and modulus properties, suitable elastomers also should have a tensile strength greater than about 500 psi or greater than about 1,000 psi, and a tear strength of greater than about 50 lbs/inch or greater than about 80 lbs/inch.

Exemplary bioerodible, biocompatible elastomers include, but are not limited to, elastomeric copolymers of ε-caprolactone and glycolide with a mole ratio of ε-caprolactone to glycolide of from about 35/65 to about 65/35 or from about 35/65 to about 45/55; elastomeric copolymers of ε-caprolactone and lactide where the mole ratio of ε-caprolactone to lactide is from about 35/65 to about 65/35 or from about 35/65 to about 45/55; elastomeric copolymers of lactide and glycolide where the mole ratio of lactide to glycolide is from about 95/5 to about 85/15; elastomeric copolymers of p-dioxanone and lactide where the mole ratio of p-dioxanone to lactide is from about 40/60 to about 60/40; elastomeric copolymers of ε-caprolactone and p-dioxanone where the mole ratio of ε-caprolactone to p-dioxanone is from about 30/70 to about 70/30; elastomeric copolymers of p-dioxanone and trimethylene carbonate where the mole ratio of p-dioxanone to trimethylene carbonate is from about 30/70 to about 70/30; elastomeric copolymers of trimethylene carbonate and glycolide where the mole ratio of trimethylene carbonate to glycolide is from about 30/70 to about 70/30; elastomeric copolymers of trimethylene carbonate and lactide where the mole ratio of trimethylene carbonate to lactide is from about 30/70 to about 70/30, or blends thereof.

Hydrogel polymers are hydrophilic, three-dimensional networks that absorb or adsorb large amounts of water or biological fluids, while maintaining their distinct three-dimensional structure. Hydrogel polymers such as alginate, coral, agarose, fibrin, collagen, cartilage, hydroxyapatite, calcium phosphate, polylactic acid (PLA), polyglycolic acid (PGA) or their copolymer (PLGA), chitosan, and polyethylene glycol-based polymers (peg-based polymers) such as polyethylene glycol diacrylate, polyethylene glycol dimethacrylate and mixtures thereof are also appropriate for use. A polyethylene glycol diacrylate or dimethacrylate monomer can have a molecular weight of about 1000 to about 100,000 daltons and about 2000 to about 5000 daltons.

Polyethylene glycol-based hydrogel polymers have certain advantages for tissue engineering applications because of their biocompatibility and their demonstrated capacity to support growth and differentiation of stem cells into multiple lineages. In one embodiment, a matrix can be formed by polymerization of polyethylene glycol diacrylate monomer [MW 3400; Shearwater Polymers, Huntsville, Ala.]. In another embodiment, aliphatic polyesters are synthesized in a ring-opening polymerization. The monomers generally are polymerized in the presence of an organometallic catalyst and an initiator at elevated temperatures. In one embodiment, the organometallic catalyst is tin based, e.g., stannous octoate, and is present in the monomer mixture at a molar ratio of monomer to catalyst ranging from about 10,000/1 to about 100,000/1. The initiator is typically an alkanol (including diols and polyols), a glycol, a hydroxyacid, or an amine, and is present in the monomer mixture at a molar ratio of monomer to initiator ranging from about 100/1 to about 5000/1. The polymerization typically is carried out at a temperature range from about 80° C. to about 240° C., or from about 100° C. to about 220° C., until the desired molecular weight and viscosity are achieved.

One of ordinary skill in the art will appreciate that the selection of a suitable polymer or copolymer for forming the disclosed matrices depends on several factors. The more relevant factors in the selection of the appropriate polymer(s) that is used to form the matrix include biodegradation kinetics; in viva mechanical performance; cell response to the material in terms of cell attachment, proliferation, migration and differentiation; and biocompatibility.

Other relevant factors that, to some extent, dictate the in vitro and in vivo behavior of the polymer include the chemical composition, spatial distribution of the constituents, the molecular weight of the polymer and the degree of crystallinity.

The ability of the material substrate to resorb in a timely fashion in the body environment is critical. But the differences in the degradation time under in vivo conditions also can be the basis for combining two different copolymers. For example, a copolymer of 35/65 ε-caprolactone and glycolide (a relatively fast degrading polymer) is blended with 40/60 ε-caprolactone and lactide copolymer (a relatively slow degrading polymer) to form the matrix. In one embodiment, the rate of resorption of the matrix by the body approximates the rate of replacement of the matrix by tissue. That is to say, the rate of resorption of the matrix relative to the rate of replacement of the matrix by tissue must be such that the structural integrity required of the matrix is maintained for the required period of time. Thus, the disclosed matrices advantageously balance the properties of bioerodibility, resorption and structural integrity over time and the ability to facilitate tissue in-growth, each of which is desirable, useful or necessary in tissue healing and soft tissue reconstruction or augmentation.

In another embodiment, it can be desirable to use polymer blends to form structures which transition from one composition to another composition in a gradient-like architecture. Matrices having this gradient-like architecture are particularly advantageous in tissue healing and soft tissue reconstruction or augmentation.

In one embodiment, the matrix can be made by a polymer-solvent phase separation technique, such as lyophilization. Generally, however, a polymer solution can be separated into two phases by any one of four techniques: (a) thermally induced gelation/crystallization; (b) non-solvent induced separation of solvent and polymer phases; (c) chemically induced phase separation, and (d) thermally induced spinodal decomposition. The polymer solution is separated in a controlled manner into either two distinct phases or two bicontinuous phases. Subsequent removal of the solvent phase usually leaves a porous matrix having a density less than that of the bulk polymer and pores in the micrometer ranges.

The steps involved in the preparation of these matrices can include choosing the appropriate solvents for the polymers to be lyophilized and preparing a homogeneous solution of the polymer in the solution. The polymer solution then can be subjected to a freezing and a vacuum drying cycle. The freezing step phase-separates the polymer solution and the vacuum drying step removes the solvent by sublimation and/or drying, thus leaving a porous, polymer matrix, or an interconnected, open-cell, porous matrix.

Suitable solvents that can be used in the preparation of the disclosed matrices include, but are not limited to, hexafluoroisopropanol (HFIP), cyclic ethers (e.g., tetrahydrofuran (THF) and dimethylene fluoride (DMF)), acetone, methylethyl ketone (MEK), 1,4-dioxane, dimethylcarbonate, benzene, toluene, N-methyl pyrrolidone, dimethylformamide, chloroform, and mixtures thereof. A homogeneous solution of the polymer in the solvent is prepared using standard techniques.

The applicable polymer concentration or amount of solvent that can be utilized can vary with each system. Generally, the amount of polymer in the solution can vary from about 0.01% to about 90% by weight or from about 0.1% to about 30% by weight, depending on factors such as the solubility of the polymer in a given solvent and the final properties desired in the particular matrix.

In one embodiment, solids can be added to the polymer-solvent system to modify the composition of the resulting matrix surfaces. As the added particles settle out of solution to the bottom surface, regions can be created that can have the composition of the added solids, not the matrix polymeric material. Alternatively, the added solids can be more concentrated in desired regions (i.e., near the top, sides, or bottom) of the resulting matrix, thus causing compositional changes in all such regions.

A variety of types of solids can be added to the polymer-solvent system. In one embodiment, the solids are of a type that will not react with the polymer or the solvent. Generally, the added solids can have an average diameter of less than about 1 mm and in certain embodiments can have an average diameter of about 50 to about 500 microns. In particular embodiments, the solids can be present in an amount such that they constitute from about 1 to about 50 volume percent of the total volume of the particle and polymer-solvent mixture (wherein the total volume percent equals 100 volume percent).

Exemplary solids include, but are not limited to, leachable solids for pore creation and particles of bioerodible polymers not soluble in the solvent system that are effective as reinforcing materials or to create pores as they are degraded, non-bioerodible materials, and biologically-derived bioerodible materials.

Suitable leachable solids include, without limitation, non-toxic leachable materials such as salts (e.g., sodium chloride, potassium chloride, calcium chloride, sodium tartrate, sodium citrate, and the like), biocompatible mono and disaccharides (e.g., glucose, fructose, dextrose, maltose, lactose and sucrose), polysaccharides (e.g., starch, alginate, chitosan) and water soluble proteins (e.g., gelatin and agarose). The leachable materials can be removed by immersing the matrix with the leachable material in a solvent in which the particle is soluble for a sufficient amount of time to allow leaching of substantially all of the particles, but which does not dissolve or detrimentally alter the matrix. In one embodiment, the matrix can be dried after the leaching process is complete at a low temperature and/or vacuum to minimize hydrolysis of the matrix unless accelerated degradation of the matrix is desired.

In certain embodiments, mammalian cells can be seeded or cultured with the disclosed matrices prior to implantation. Cells that can be seeded or cultured on the matrices include, but are not limited to, bone marrow cells, stem cells, mesenchymal stem cells, synovial derived stem cells, embryonic stem cells, umbilical cord blood cells, umbilical Wharton's jelly cells, precursor cells derived from adipose tissue, bone marrow derived progenitor cells, peripheral blood progenitor cells, stem cells isolated from adult tissue and genetically transformed cells or combinations of the above cells. The cells can be seeded on the matrices for a short period of time (<1 day) just prior to implantation, or cultured for a longer (>1 day) period to allow for cell proliferation and extracellular matrix synthesis within the seeded matrix prior to implantation.

In one embodiment, stem cells are seeded or cultured on the disclosed matrices. De novo synthesis of soft tissue prepared from stem cells within a matrix provides constructs for repair, augmentation or reconstruction of soft tissue. Adult stem cells are capable of differentiating into all connective tissue-forming cell lineages including adipose tissue. Stem cells can be obtained with minimally invasive procedures from bone marrow or other sources in the body, are highly expandable in culture, and can be readily induced to differentiate into adipose tissue-forming cells after exposure to a well-established adipogenic inducing supplement (Pittenger et al., Caplan, 2003).

In one embodiment stem cells are derived from bone marrow cells. In addition, adipose tissue is an especially rich source of stem cells. In both human and animal studies, processed lipoaspirate (PLA) contains stem cells at a frequency of at least 0.1%, and more typically greater than 0.5%. In some instances, PLA can be obtained which contains between about 2-12% stem cells. The amount of stem cells obtained from PLA can be substantially greater than the published frequency of 1 in 100,000 (0.001%) from marrow. Furthermore, collection of adipose tissue is associated with lower morbidity than collection of a similar volume of marrow. In addition, adipose tissue contains endothelial precursor cells, which are capable of providing therapy to patients.

When utilized as a source of stem cells, adipose tissue can be obtained by any method known to a person of ordinary skill in the art. For example, adipose tissue can be removed from a patient by suction-assisted lipoplasty, ultrasound-assisted lipoplasty, and excisional lipectomy. In addition, the procedures can include a combination of such procedures. Suction assisted lipoplasty can be desirable to remove the adipose tissue from a patient as it provides a minimally invasive method of collecting tissue with minimal potential for stem cell damage that can be associated with other techniques, such as ultrasound assisted lipoplasty. The adipose tissue should be collected in a manner that preserves the viability of the cellular component and that minimizes the likelihood of contamination of the tissue with potentially infectious organisms, such as bacteria and/or viruses.

For some applications preparation of the active cell population can require depletion of the mature fat-laden adipocyte component of adipose tissue. This is typically achieved by a series of washing and disaggregation steps in which the tissue is first rinsed to reduce the presence of free lipids (released from ruptured adipocytes) and peripheral blood elements (released from blood vessels severed during tissue harvest), and then disaggregated to free intact adipocytes and other cell populations from the connective tissue matrix.

Disaggregation can be achieved using any conventional techniques or methods, including mechanical force (mincing or shear forces), enzymatic digestion with single or combinatorial proteolytic enzymes, such as collagenase, trypsin, lipase, liberase H1 and pepsin, or a combination of mechanical and enzymatic methods. For example, the cellular component of the intact tissue fragments can be disaggregated by methods using collagenase-mediated dissociation of adipose tissue, similar to the methods for collecting microvascular endothelial cells in adipose tissue, as known to those of skill in the art. Additional methods using collagenase that can be used are also known to those of skill in the art. Furthermore, methods can employ a combination of enzymes, such as a combination of collagenase and trypsin or a combination of an enzyme, such as trypsin, and mechanical dissociation.

The active cell population (processed lipoaspirate) can then be obtained from the disaggregated tissue fragments by reducing the presence of mature adipocytes. Separation of the cells can be achieved by buoyant density sedimentation, centrifugation, elutriation, differential adherence to and elution from solid phase moieties, antibody-mediated selection, differences in electrical charge; immunomagnetic beads, fluorescence activated cell sorting (FACS), or other means.

In one embodiment, solutions contain collagenase at concentrations from about 10 µg/ml to about 50 µg/ml and are incubated at from about 30° C. to about 38° C. for from about 20 minutes to about 60 minutes. A particular concentration, time and temperature is 20 µg/ml collagenase (Blendzyme 1, Roche) incubated for 45 minutes, at about 37° C.

Following disaggregation the active cell population can be washed/rinsed to remove additives and/or by-products of the disaggregation process (e.g., collagenase and newly-released free lipid). The active cell population could then be concentrated by centrifugation. In one embodiment, the cells are concentrated and the collagenase removed by passing the cell population through a continuous flow spinning membrane system or the like, such as, for example, the system disclosed in U.S. Pat. Nos. 5,034,135 and 5,234,608, which are incorporated by reference herein.

In addition to the foregoing, there are many post-wash methods that can be applied for further purifying the active cell population. These include both positive selection (selecting the target cells), negative selection (selective removal of unwanted cells), or combinations thereof. In another embodiment the cell pellet could be resuspended, layered over (or under) a fluid material formed into a continuous or discontinuous density gradient and placed in a centrifuge for separation of cell populations on the basis of cell density. In a similar embodiment continuous flow approaches such as apheresis and elutriation (with or without counter-current) could be used. Adherence to plastic followed by a short period of cell expansion has also been applied in bone marrow-derived adult stem cell populations. This approach uses culture conditions to preferentially expand one population while other populations are either maintained (and thereby reduced by dilution with the growing selected cells) or lost due to absence of required growth conditions. The active cells that have been concentrated, cultured and/or expanded can be incorporated into disclosed matrices.

In one embodiment, stem cells are harvested, the harvested cells are contacted with an adipogenic medium for a time sufficient to induce differentiation into adipocytes, and the adipocytes are loaded onto a biocompatible matrix which is implanted. In additional embodiments, at least some of the stem cells can be differentiated into adipocytes so that a mixture of both cell types is initially present that changes over time to substantially only adipocytes, with stem cells being present in small to undetectable quantities. Adipose tissue is fabricated in vivo by the stem cells or prepared ex vivo by the stem cells.

Cells can be integrated with the disclosed matrices using a variety of methods. For example, the matrices can be submersed in an appropriate growth medium for the cells of interest, and then directly exposed to the cells. The cells are allowed to proliferate on the surface and interstices of the matrix. The matrix is then removed from the growth medium, washed if necessary, and implanted. Alternatively, the cells can be placed in a suitable buffer or liquid growth medium and drawn through the matrix by using vacuum filtration.

Cells can also be admixed with a precursor of the matrix, and the matrix can then be constructed around the cells, capturing at least some of the cells within the matrix network. In another embodiment, the cells of interest are dissolved into an appropriate solution (e.g., a growth medium or buffer) and then sprayed onto a matrix while the matrix is being formed by electrospinning. This method is particularly suitable when a highly cellularized matrix is desired. Cells can also be electrosprayed onto the matrix during electrospinning. As presently described, electrospraying involves subjecting a cell-containing solution with an appropriate viscosity and concentration to an electric field sufficient to produce a spray of small charged droplets of solution that contain cells.

In one embodiment, the matrix is a biocompatible, resorbable polyurethane polymer matrix with a pore size of about 20 microns to about 350 microns that includes stem cells derived from bone marrow and/or adipose tissue. This embodiment can also include an adipogenic agent dispersed within the matrix. The adipogenic agent can be, without limitation, pioglitazone, growth factors of the β-family, prostaglandins, ciglitazone, dexamethasone or combinations thereof.

Furthermore, the disclosed matrices can be used as a therapeutic agent, or drug, release depot. The variety of different therapeutic agents that can be used in conjunction with the disclosed matrices is vast. In general, therapeutic agents that can be administered via the disclosed matrices include, without limitation: anti-rejection agents, analgesics, anti-oxidants, anti-apoptotic agents such as erythropoietin, anti-inflammatory agents such as anti-tumor necrosis factor α, and combinations thereof.

To form such a release depot, the polymer could be mixed with a therapeutic agent prior to forming the matrix. Alternatively, a therapeutic agent could be coated onto the polymer, in one embodiment with a pharmaceutically acceptable carrier. Any pharmaceutical carrier can be used that does not dissolve the polymer. The therapeutic agent can be present as a liquid, a finely divided solid, or any other appropriate physical form. Typically, but optionally, the depot can include one or more additives, such as diluents, carriers, excipients, stabilizers or the like.

The amount of therapeutic agent can depend on the particular agent being employed and the particular goal of providing the therapeutic agent. Typically, the amount of agent can represent about 0.001 percent to about 70 percent, about 0.001 percent to about 50 percent, or about 0.001 percent to about 20 percent by weight of the depot. The quantity and type of polymer incorporated into the therapeutic agent delivery depot can vary depending on the release profile desired and the amount of agent employed.

In another embodiment, a disclosed cell-seeded matrix can undergo gradual degradation (mainly through hydrolysis) with concomitant release of the dispersed therapeutic agent for a sustained or extended period. This can result in prolonged delivery, e.g. over about 1 to about 5,000 hours or over about 2 to about 800 hours, of effective amounts, e.g. from about 0.0001 mg/kg/hour to about 10 mg/kg/hour, of the therapeutic agent. This dosage form can be administered as is necessary depending on the particular situation at hand. Following this or similar procedures, those skilled in the art will be able to prepare a variety of formulations.

In one embodiment, the structure of the matrix should be effective to facilitate tissue ingrowth. One tissue ingrowth-promoting matrix includes pores of a sufficient size to permit cell growth therein. An effective pore size is one in which the pores have an average diameter in the range of from about 10 to about 1,000 microns, or from about 20 to about 90 microns.

In another embodiment, the matrix is a biocompatible, resorbable polyurethane polymer matrix with a pore size of about 20 microns to about 350 microns that includes stem cells derived from bone marrow and/or adipose tissue, and an adipogenic agent, a nutrient medium, optionally a growth factor, and at least one antibiotic. Exemplary adipogenic agents, nutrients and antibiotics include, without limitation, amphotericin B, ciglitazone, biotin, dexamethasone, gentamicin, insulin, 3-isobutyl-1-methylxanthine, L-thyroxine or combinations thereof.

In another embodiment, the matrix is biocompatible, bioerodible polyurethane formulation that can incorporate polycaprolactone soft segments. In this embodiment, pores can range in size from about 20 microns to about 350 microns. The matrix can be seeded with one or more mammalian cell types and/or therapeutic agents.

As stated, the disclosed matrices have many potential uses including, without limitation, as promoting closure and protection of incision sites; supporting the lower pole position of breast implants; and providing a partial or complete covering of breast implants, for example, textured breast implants, to provide a beneficial interface with host tissue and to reduce the potential for malpositioning or capsular contracture.

Unless otherwise indicated, all numbers expressing quantities or properties and so forth used in the specification and claims are to be understood as being modified in all instances by the term "about." Accordingly, unless indicated to the contrary, the numerical parameters set forth in the specification and attached claims are approximations that can vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. It is anticipated that one or more members of a group can be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that can be employed are within the scope of the invention. Thus, by way of example, but not of limitation, alternative configurations of the present invention can be utilized in accordance with the teachings herein. Accordingly, the present invention is not limited to that precisely as shown and described.

What is claimed is:

1. A medical implant comprising:
   a breast prosthesis; and
   a matrix on said breast prosthesis, the matrix comprising a resorbable or bioerodible polymer component and a cellular component, wherein the polymer component comprises polycaprolactone soft segments having an amorphous rubbery phase, the matrix having a porosity conducive to cell growth and capable of providing a beneficial interface between the prosthesis and host tissue to enhance biocompatibility and reducing the potential for malpositioning or capsular contracture.

2. The implant of claim 1 wherein the cellular component comprises stem cells.

3. The implant of claim 1 wherein the cellular component comprises adipose cells.

4. The implant of claim 1 wherein the cellular component comprises stem cells and adipose cells.

5. The implant of claim 1 wherein the matrix forms at least a partial covering on said breast prosthesis.

6. The implant of claim 1 wherein the matrix forms a complete covering of said breast prosthesis.

7. The implant of claim 1 wherein the matrix has a pore size diameter of about 10 to about 1000 microns.

8. The implant of claim 1 wherein the matrix has a pore size diameter of from about 20 to about 90 microns.

* * * * *